(12) United States Patent  
Sawanaga

(10) Patent No.: US 8,351,566 B2
(45) Date of Patent: Jan. 8, 2013

(54) PET DEVICE

(75) Inventor: Yuuji Sawanaga, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 301 days.

(21) Appl. No.: 12/633,282

(22) Filed: Dec. 8, 2009

(65) Prior Publication Data

US 2010/0166137 A1 Jul. 1, 2010

(30) Foreign Application Priority Data

Dec. 25, 2008 (JP) ................................. 2008-331408

(51) Int. Cl.
*G01N 23/00* (2006.01)

(52) U.S. Cl. ..................... 378/19; 250/363.04

(58) Field of Classification Search ............... 378/4, 15, 378/19, 63; 250/363.03, 363.04; 382/131
See application file for complete search history.

(56) References Cited

U.S. PATENT DOCUMENTS

| | | | |
|---|---|---|---|
| 6,976,784 B2 * | 12/2005 | Kojima et al. ................ 378/197 |
| 7,154,096 B2 | 12/2006 | Amano |
| 7,291,840 B2 * | 11/2007 | Fritzler et al. ........... 250/363.05 |
| 7,570,791 B2 * | 8/2009 | Frank et al. ................... 382/132 |
| 7,807,981 B2 * | 10/2010 | Frach et al. ................ 250/492.1 |
| 2004/0138920 A1 | 7/2004 | Sawanaga et al. |
| 2007/0057191 A1 * | 3/2007 | Ueno et al. ............... 250/370.09 |

FOREIGN PATENT DOCUMENTS

| JP | 2005-121530 | 5/2005 |
| JP | 2006-192286 | 7/2006 |

* cited by examiner

*Primary Examiner* — Jurie Yun
(74) *Attorney, Agent, or Firm* — Oblon, Spivak, McClelland, Maier & Neustadt, L.L.P.

(57) ABSTRACT

A gantry has a cylindrical shape and rotates around a subject on a top panel about the body axis. An X-ray irradiating part is arranged inside the gantry and emits an X-ray. An X-ray detector is arranged at a position facing the X-ray irradiating part and detects the X-ray transmitted through the subject. PET detectors are arranged in two separate regions facing the rotation center and detect γ-rays emitted from the positron-emitting nuclides. A moving mechanism moves the top panel and the gantry relatively to each other. An X-ray CT image generator generates an X-ray CT image of the subject based on the result of detection by the X-ray detector. A PET image generator generates a PET image of the subject based on the γ-rays detected by the PET detectors on the circumference in accordance with rotation of the gantry.

18 Claims, 3 Drawing Sheets

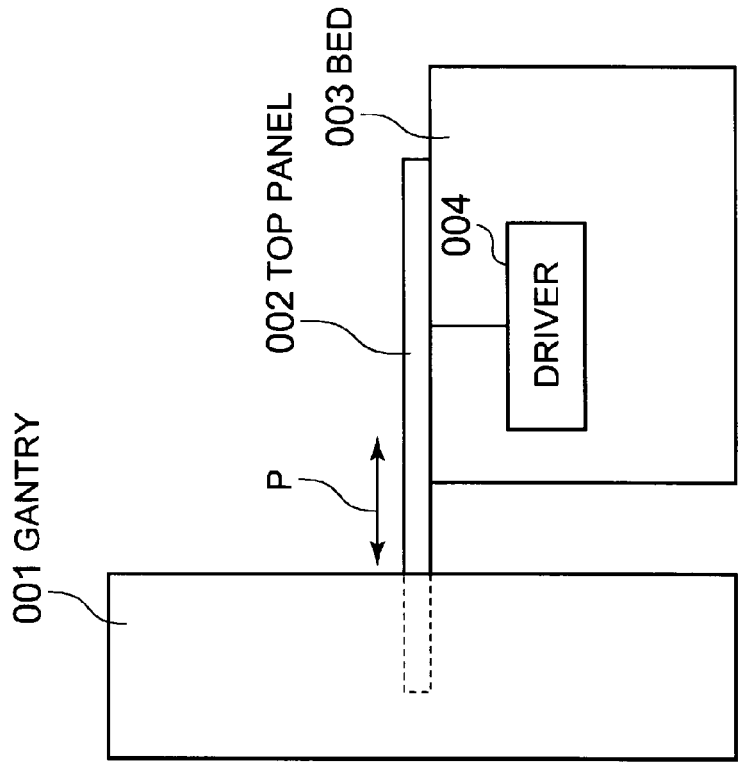
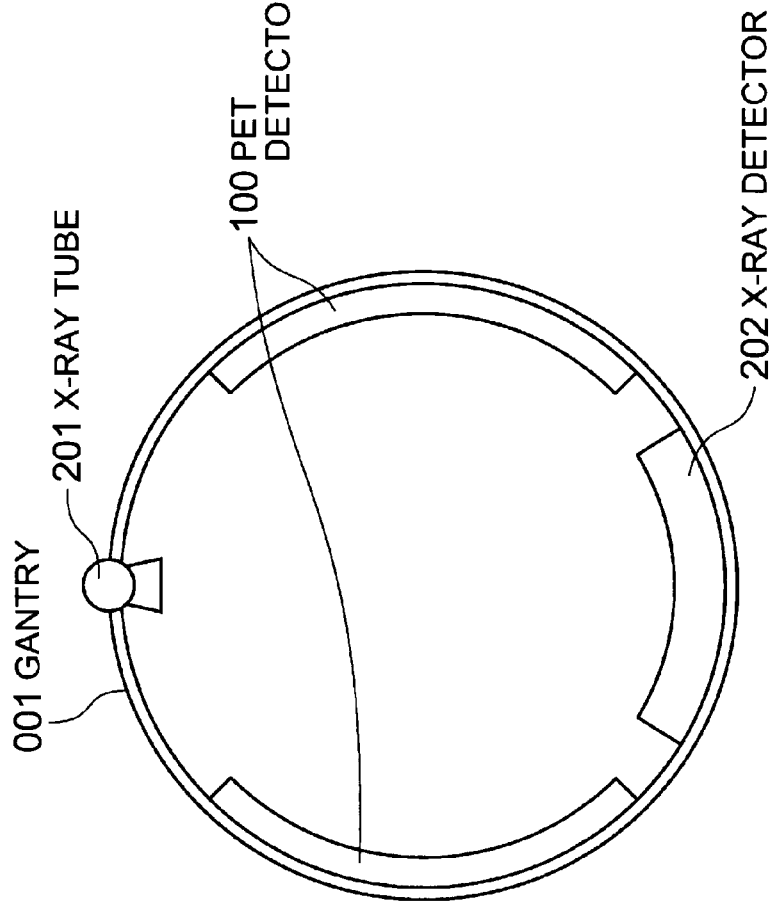

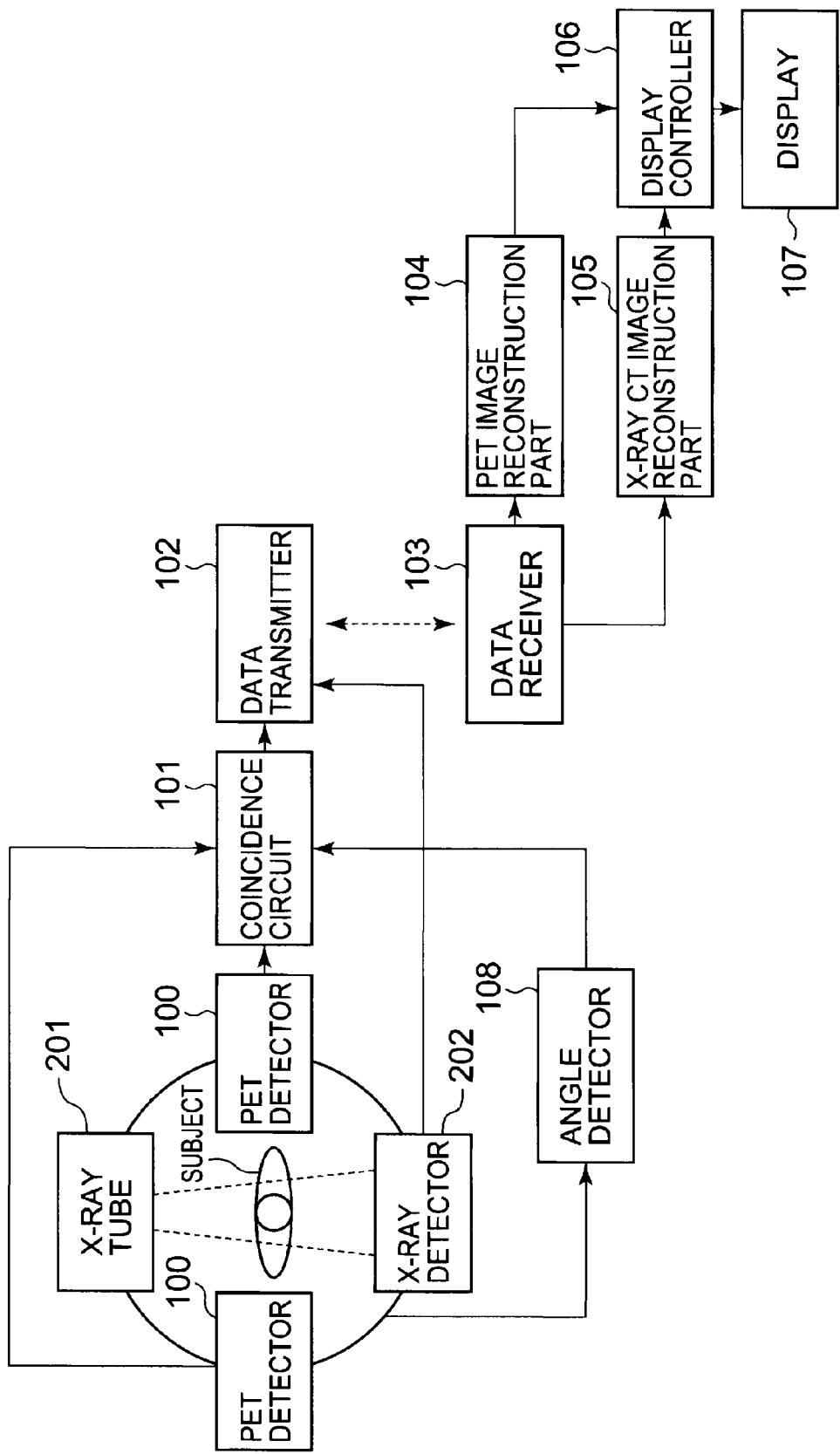

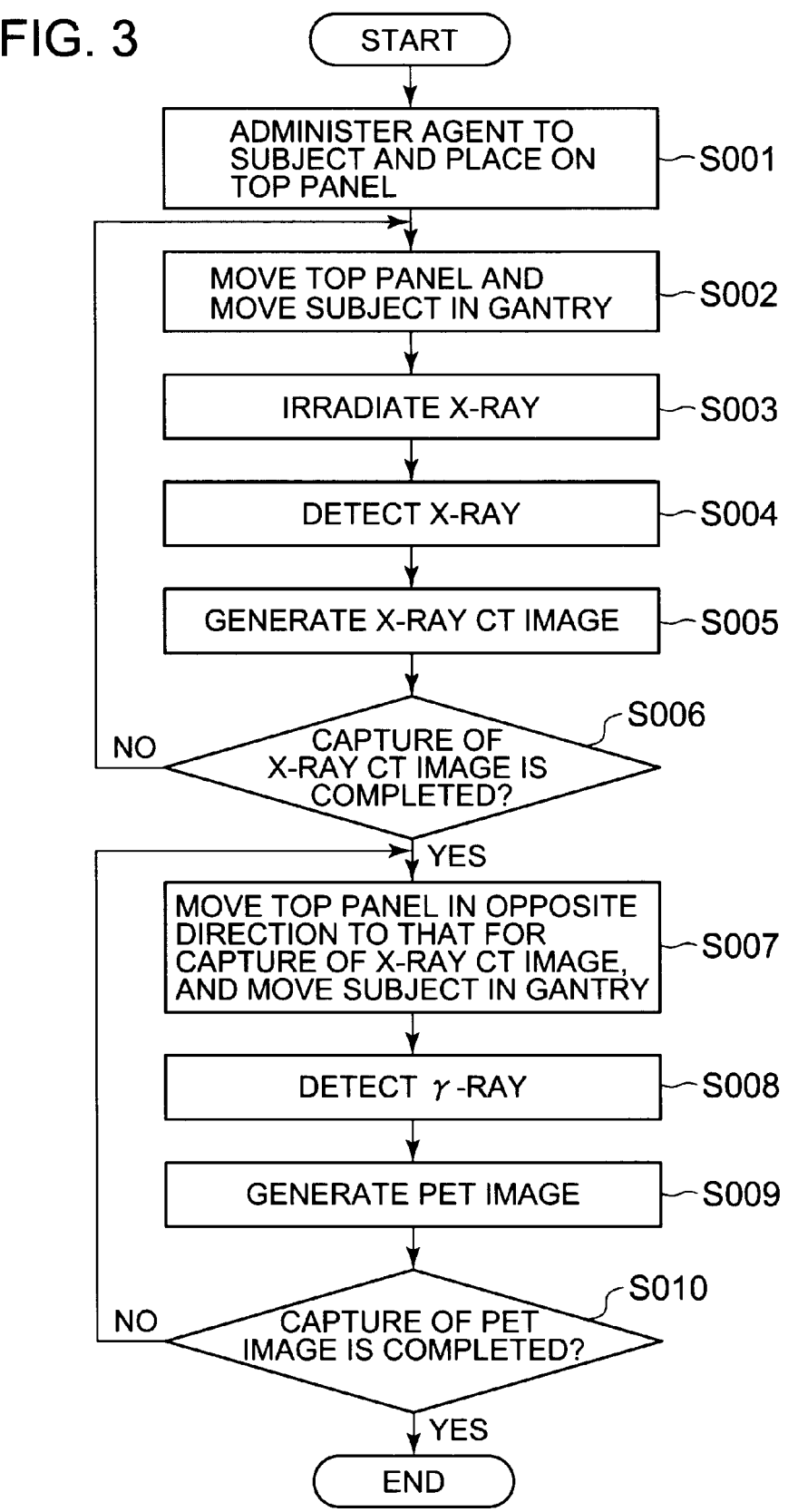

PET DEVICE

BACKGROUND OF THE INVENTION

1. Field of the Invention

The present invention relates to a PET device (Positron Emission Tomography device) that coincidentally measures a pair of γ-rays emitted from an agent labeled with positron nuclides and performs a scan for obtaining a tomographic image at a site of interest.

To be specific, the present invention relates to a PET device used in combination with an X-ray CT (Computed Tomography) device.

2. Description of the Related Art

A PET (Positron Emission Tomography) test is a very useful technique for early detection of cancer. However, a PET image represents the accumulation and distribution state of nuclides, but does not show the location thereof in tissues within a human body. As a device for obtaining the shape of the tissues within the human body, there is a device in which a PET test and an X-ray CT test of imaging the distribution of X-ray absorption coefficients are used in combination. A method of executing a precise diagnosis by observing a fusion image composed by superimposing a PET image and an X-ray CT image by this device has been practically used (refer to Japanese Unexamined Patent Application Publication No. 2005-121530, for example).

The device in which the PET device and the X-ray CT device are combined has a top panel held on a bed so as to be movable horizontally, and a cylindrical PET gantry (a PET detector) and a CT gantry (a CT detector) through which a subject placed on the top panel can pass. In the order of proximity from the top panel, the CT gantry and the PET gantry are arranged close to each other. As the top panel moves, data of a PET image and an X-ray CT image of the same plane of the subject are acquired on each scan plane. After a PET image and an X-ray CT image are obtained through image processing by an image processor (not shown) composed of a computer and a memory, these images are superimposed and composed, and displayed as a fusion image on an image display.

Further, there is a conventional system known as SPECT (Single Photon Emission Computed Tomography), which is configured by a rotating part and a fixed part as in a CT device. With regard to this SPECT system, there is a technique of capturing an image by rotating a gantry (refer to Japanese Unexamined Patent Application Publication No. 2006-192286, for example). However, agents used for a PET image and a SPECT image are different from each other. Two γ-rays are generated from the agent used for a PET image. On the other hand, an image is generated with particles of only one γ-ray generated from the agent used for a SPECT image. Therefore, the SPECT system as a mechanism merely needs to detect particles of a γ-ray travelling in one direction, and there is no need to arrange γ-ray detectors at the facing positions. On the contrary, the PET device needs to detect particles of a pair of γ-rays travelling in opposing directions at 180°, and it is always necessary to arrange γ-ray detectors at the facing positions.

Besides, since a SPECT image has lower resolution than a PET image, the SPECT image is suitable for a measurement of the blood flow rate in the brain but hard to be used for a measurement of the distribution of glucose metabolism at a spot where cancer develops.

In the technique described in Japanese Unexamined Patent Application Publication No. 2005-121530, there is a certain distance between the PET detector and the CT detector as described above.

Therefore, there is a need to make the top panel protrude largely from the bed when performing a PET test, which causes the top panel to bend largely. When the top panel thus bends largely, the position of the subject is displaced from the center for capturing an image, and therefore, the quality of the PET image deteriorates. Accordingly, it is difficult to generate a PET image of favorable image quality.

The technique described in Japanese Unexamined Patent Application Publication No. 2006-192286 is a technique for the SPECT device. The SPECT device and the PET device are largely different in resolution, and the SPECT device does not have resolution required in the PET device. Therefore, it is difficult to implement the technique described in Japanese Unexamined Patent Application Publication No. 2006-192286 as it is in the PET device. Moreover, also in Japanese Unexamined Patent Application Publication No. 2006-192286, the SPECT device and the X-ray CT device are arranged in separate gantries. Therefore, it is difficult to reduce a difference in bend of the top panel between capturing images by the devices.

Further, since a conventional PET device is provided with γ-ray detectors on the entire circumference inside the cylindrical PET gantry, the cost is high. Furthermore, since a large number of detectors are arranged on the entire circumference inside the PET gantry, it is relatively difficult to manage the properties of the detectors uniformly.

Besides, it takes much time for an investigation when a failure occurs in the detectors.

SUMMARY OF THE INVENTION

The present invention was made in consideration of such circumstances, and an object of the present invention is to provide a PET device that has fewer PET detectors (γ-ray detectors) and can perform capture of a PET image at substantially the same position as for capture of an X-ray CT image.

In a first aspect of the present invention, a PET device comprises: a top panel on which a subject to which an agent labeled with positron-emitting nuclides have been administered is placed; a cylindrical gantry configured to rotate around the subject about a body axis of the subject; an X-ray irradiating part arranged inside the gantry and configured to irradiate an X-ray; an X-ray detector arranged at a position facing the X-ray irradiating part inside the gantry and configured to detect the X-ray having been transmitted through the subject; two PET detectors arranged in two regions facing a rotation center inside the gantry and configured to detect γ-rays emitted from the positron-emitting nuclides; a moving mechanism configured to move the top panel and the gantry relatively to each other; an X-ray CT image generator configured to generate an X-ray CT image of an inside of the subject based on a result of detection by the X-ray detector; and a PET image generator configured to generate a PET image of the inside of the subject based on the γ-rays detected by the PET detectors on a circumference in accordance with rotation of the gantry.

According to the first aspect, since the X-ray detector and the PET detectors are arranged inside one gantry, it is possible to arrange the X-ray detector and the PET detectors close to each another, and a transfer distance of the top panel at the time of capture of an X-ray CT image becomes substantially the same as that at the time of capture of a PET image. Consequently, it is possible to reduce bend of the top panel during capture of an image.

Further, the PET device according to the first aspect is provided with the two PET detectors at facing positions within the gantry and configured to rotate the PET detectors and capture an image.

Consequently, it is possible to reduce the number of γ-ray detectors included in the PET detectors and to detect the γ-rays on the entire circumference by rotation, and therefore, it is possible to generate an accurate PET image.

BRIEF DESCRIPTION OF THE DRAWINGS

FIG. 1A is a schematic cross-sectional view of a PET device according to a first embodiment, and FIG. 1B is a schematic side view of the PET device according to the first embodiment.

FIG. 2 is a block diagram of the PET device according to the first embodiment.

FIG. 3 is a flow chart of capture of an X-ray CT image and a PET image by the PET device according to the first embodiment.

DETAILED DESCRIPTION OF THE EMBODIMENTS

[First Embodiment]

A PET device according to a first embodiment of the present invention will be described. FIG. 1A is a schematic cross-sectional view of the PET device according to the present embodiment. FIG. 1B is a schematic side view of the PET device according to the present embodiment. FIG. 2 is a block diagram showing the function of the PET device according to the present embodiment.

As shown in FIG. 1B, the PET device according to the present embodiment has a gantry 001, a top panel 002, and a bed 003.

The bed 003 supports the top panel 002 so as to move back and forth in the longer direction, namely, so as to be movable in a direction indicated by an arrow P in FIG. 1B. The bed 003 is provided with a driver 004 configured to move the top panel 002 in the arrow P direction. This driver 004 is equivalent to the "moving mechanism" of the present invention.

The top panel 002 is a member on which the subject is placed.

When the subject is placed, a direction connecting the head and feet of the subject is set in the longer direction of the top panel 002, and a direction connecting both the sides of the subject is set in the shorter direction of the top panel 002. In the following description, a direction toward the gantry 001 indicated by the arrow P in FIG. 1B will be referred to as a "forward direction," and a direction away from the gantry 001 will be referred to as a "backward direction." Further, a length in the longer direction of the top panel 002 will be referred to as a "length in the arrow P direction" or a "width in the arrow P direction." As moving in the forward direction, the top panel 002 moves away from the bed 003. Consequently, the top panel 002 loses the underlying support and bends in some degree.

The gantry 001 is installed at a longitudinal position of the top panel 002. The gantry 001 is formed into a cylindrical shape and arranged so that the hole of the cylindrical gantry 001 is orthogonal to the longer direction of the top panel 002. When the top panel 002 moves in the forward direction, the top panel 002 is inserted into the hole of the gantry 001.

On the cylindrical inner face of the gantry 001, as shown in FIG. 1A, PET detectors 100, an X-ray tube 201, and an X-ray detector 202 paired with the X-ray tube 201 are arranged. The gantry 001 rotates about an axis positioned in parallel to the longer direction of the top panel 002 (the axis is substantially overlapped with the body axis of the subject placed on the top panel). The gantry 001 rotates at the time of capture of an X-ray CT image and at the time of capture of a PET image. In the present embodiment, the gantry 001 rotates at a rate of 0.5 second per rotation. Although the capture of a PET image is performed at the same rotation rate as the typical capture of an X-ray CT image in the present embodiment, the rotation is sufficient as far as the γ-rays can be detected at 360° on the entire circumference at the time of capture of a PET image, and there is no particular limitation on the rotation rate.

The basis of the following description is that capture of a PET image is usually performed after capture of an X-ray CT image ends and the capture of an X-ray CT image and the capture of a PET image are not performed simultaneously. To be specific, the capture of an X-ray CT image is firstly performed by rotating the gantry 001 to move the top panel 002 in the forward direction and performing irradiation and detection of an X-ray while inserting the top panel 002 into the hole of the gantry 001, and the capture of a PET image is subsequently performed by rotating the gantry 001 to move the top panel 002 in the backward direction and performing detection of γ-rays while inserting the top panel 002 into the hole of the gantry 001. However, the method for capturing a PET image is not limited on the above method. For example, a PET image may be captured by, after moving the top panel 002 in the backward direction, moving the top panel 002 in the forward direction again while rotating the gantry 001, and performing detection of γ-rays while inserting the top panel 002 into the hole of the gantry 001 again.

The PET detectors 100 are arranged in two separate regions, respectively, as shown in FIG. 1A. These two separate regions are arranged on substantially the same circumference as a circumference on which the X-ray tube 201 and the X-ray detector 202 described later are arranged. Here, "on substantially the same circumference" represents that the center line of the width in the arrow P direction of the PET detector 100 substantially coincides with the center line of the width in the arrow P direction of the X-ray detector 202. Although the widths in the arrow P direction of the PET detector 100 and the X-ray detector 202 are not specifically shown in the drawing, the widths do not need to be equal, and either width may be longer as far as the center lines of the widths in the arrow P direction substantially coincide with each other.

In the most common configuration, the PET detectors 100 are respectively provided with a number of scintillator arrays. The PET detector 100 is arranged in each of the abovementioned two regions.

Each of the scintillator arrays is a γ-ray detector. The PET detectors 100 are arranged so that each scintillator of the one PET detector 100 and each scintillator of the other PET detector 100 are paired and located at 180° from each other. The PET detectors 100 are located so as not to be exposed to the X-ray irradiated from the X-ray tube 201. It is more preferable if a region to arrange each of the PET detectors 100 is broader in the circumferential direction of the gantry 001 as far as not exposed to the X-ray. This is because arrangement in a broader region makes it possible to detect γ-rays with more accuracy.

Further, in the present embodiment, as shown in FIG. 1A, the PET detectors 100 are arranged symmetrically with respect to a line connecting the center of the X-ray tube 201 and the center of the X-ray detector 202. The PET detectors 100 may be arranged at any positions with respect to the X-ray tube 201 and the X-ray detector 202, as far as the PET detectors 100 do not overlap the X-ray tube 201 and the X-ray detector 202 and each of the scintillator arrays of the one PET detector 100 is located at 180° from each of the scintillator arrays of the other PET detector 100.

The scintillator array is composed of scintillator crystal that detects γ-rays and a photo multiplier tube that detects a weak optical pulse at high speed and at high sensitivity.

In response to a PET collection start signal from a PET image reconstruction part 104 described later, the PET detector 100 starts to detect γ-rays. The PET detector 100 detects, in the scintillator arrays, γ-rays radiated when positrons are emitted from radial isotopic elements administered to the subject in advance. Furthermore, the PET detector 100 outputs electric signals based on the detected γ-rays to a coincidence circuit 101.

As described above, when the gantry 001 rotates at the time of detection of γ-rays in capture of a PET image, the two regions where the PET detectors 100 are arranged also rotate around the entire circumference about the subject. Consequently, the PET detectors 100 arranged in the two separate regions of the PET device according to the present embodiment can detect γ-rays at 360° on the entire circumference, and can be configured equivalently to the PET detector 100 arranged on the entire circumference of the gantry 001.

Further, although capture of a PET image is performed while the gantry 001 is rotated in the present embodiment, another method may be employed as far as it is possible to detect γ-rays on the entire circumference about the subject. For example, the PET device may be configured to detect γ-rays at 360° on the entire circumference by repeating rotation of the gantry, stoppage of the rotation by change of an angle of the PET detector 100 with respect to the subject, and detection of γ-rays. As a specific example of this configuration, capture of an image is performed twice from two orthogonal directions because, when the length in the rotational direction of the PET detector 100 in one of the regions is a quarter of the entire circumference, the lengths of the PET detectors 100 of the two regions account for a half of the entire circumference.

An angle detector 108 is composed of an encoder or the like.

The angle detector 108 acquires the angle of the rotating PET detector 100 together with the timing. Then, the angle detector 108 transmits the angle of the PET detector 100 and the timing of the angle, to the coincidence circuit 101.

The coincidence circuit 101 determines whether the outputs from the facing two scintillator arrays are coincident. The coincidence circuit 101 detects a signal of a combination of γ-rays having entered coincidentally. Furthermore, the coincidence circuit 101 compares the timing inputted from the angle detector 108 and the timing of the combination of the detected γ-rays. Then, the coincidence circuit 101 acquires the angles of the PET detectors 100 corresponding to the detected γ-rays (namely, the angles of the PET detectors 100 when the γ-rays are detected). The coincidence circuit 101 outputs electric signals based on the detected γ-rays and the angles of the PET detectors 100 when the respective γ-rays are detected, to a data transmitter 102.

In response to a CT collecting start signal from an X-ray CT image reconstruction part 105 described later, the X-ray tube 201 starts radiation of the X-ray. The X-ray tube 201 receives supply of high voltage generated by a high-voltage generator (not shown) and radiates the X-ray to the subject. The X-ray beam radiated from the X-ray tube 201 is a fan-like or cone-like beam.

In the case of a single slice CT device, the X-ray detector 202 is configured by, for example, arranging one thousand channels of X-ray detecting elements in a row in an arched line or straight line. On the other hand, in the case of a multi slice CT device, the X-ray detector 202 is configured by arranging a plurality of X-ray detecting elements in an array in two directions orthogonal to each other (they form a slice direction and a channel direction), whereby a two-dimensional X-ray detector is formed.

In response to the CT collection start signal from the X-ray CT image reconstruction part 105 described later, the X-ray detector 202 starts detection of the X-ray. The X-ray detector 202 detects the X-ray having transmitted through the subject. The X-ray detector 202 outputs a signal based on the detected X-ray to the data transmitter 102.

The data transmitter 102 is a data transmission device that is capable of noncontact data transmission using electric waves or the like. The data transmitter 102 is attached to the gantry 001 that rotates.

The data transmitter 102 outputs the signals inputted from the coincidence circuit 101 and the X-ray detector 202 to a data receiver 103 by noncontact data transmission. A dashed-line arrow in FIG. 2 represents transmission of signals by noncontact data transmission from the data transmitter 102 to the data receiver 103.

The data receiver 103 is a data receiving device that is paired with the data transmitter 102 and capable of receiving the signals transmitted by noncontact data transmission from the data transmitter 102. The data receiver 103 is attached to a fixed part other than the gantry 001. The data receiver 103 outputs the signals received from the data transmitter 102 to the PET image reconstruction part 104.

In the present embodiment, the flow of data from the coincidence circuit 101 or X-ray detector 202 to the PET image reconstruction part 104 or X-ray CT image reconstruction part 105 will be mainly described. For this reason, of the pair of communication devices that perform noncontact data transmission, the communication device on the side of the coincidence circuit 101 or X-ray detector 202 is defined as the data transmitter 102, and the communication device on the side of the PET image reconstruction part 104 or X-ray CT image reconstruction part 105 is defined as the data receiver 103.

However, it is also possible to transmit data from the data receiver 103 to the data transmitter 102.

Thus, the data transmitter 102 and the data receiver 103 that perform noncontact data transmission are shared in both the capture of the PET image and the capture of the X-ray CT image. This noncontact data transmission includes ATM (Asynchronous Transfer Mode) communication and serial communication using light, electric waves, or the like.

The PET image reconstruction part 104 has a storage region. The PET image reconstruction part 104 previously stores a PET image capture plan that is inputted by the operator. Moreover, the PET image reconstruction part 104 receives a notice of end of the capture of an X-ray CT image from the X-ray CT image reconstruction part 105.

Then, in response to the notice of the end of the capture of the X-ray CT image, the PET image reconstruction part 104 transmits a PET collection start signal to the PET detectors 100 and the coincidence circuit 101. Furthermore, the PET image reconstruction part 104 transmits a PET collection end signal to the PET detectors 100 and the coincidence circuit

101 at the timing of end of capture of an image in accordance with the stored PET image capture plan.

The PET image reconstruction part 104 receives the signal outputted from the coincidence circuit 101, from the data receiver 103.

The PET image reconstruction part 104, based on the angles of the PET detectors 100 at the time of detection of the γ-rays, executes an image reconstruction process on the electric signals based on the γ-rays, and generates PET image data. The PET image reconstruction part 104 outputs the generated PET image data to a display controller 106. Alternatively, the PET image reconstruction part 104 may be configured to correct a PET image based on a CT value detected by the X-ray detector 202.

The X-ray CT image reconstruction part 105 has a storage region.

The X-ray CT image reconstruction part 105 previously stores an X-ray CT image capture plan inputted by the operator. The X-ray CT image reconstruction part 105 transmits the CT collection start signal and the CT collection end signal to the X-ray tube 201 and the X-ray detector 202 in accordance with the capture plan. Furthermore, the X-ray CT image reconstruction part 105 transmits a notice of end of capture of the X-ray CT image to the PET image reconstruction part 104.

The X-ray CT image reconstruction part 105 receives the signal outputted from the X-ray detector 202, from the data receiver 103. The X-ray CT image reconstruction part 105, after executing preparations such as data correction on the received electric signals, executes an image reconstruction process and generates X-ray CT image data. The X-ray image reconstruction part 105 outputs the generated X-ray CT image data to the display controller 106.

In the above description, the PET image reconstruction part 104 and the X-ray CT image reconstruction part 105 are described as separate image reconstruction parts. However, one image reconstruction part that performs reconstruction of both the images may be installed.

The display controller 106 receives the PET image data from the PET image reconstruction part 104 and the X-ray CT image data from the X-ray CT image reconstruction part 105. The display controller 106 controls a display 107 to display a PET image and an X-ray CT image based on the inputted PET image data and X-ray CT image data. The PET image and the X-ray CT image may be displayed separately or coincidentally. Moreover, in response to an instruction from the operator, the display controller 106 executes a process of superimposing the PET image and the X-ray CT image to generate a PET/CT fusion image, and controls the display 107 to display the PET/CT fusion image. The display controller 106 is equivalent to the "fusion part" of the present invention.

In the present embodiment, in order to match the position of the subject in the capture of a PET image with the position of the subject in the capture of an X-ray CT image as much as possible, the regions to arrange the PET detectors 100 are arranged on substantially the same circumference as the X-ray detector 202. In order to prevent displacement caused by bend of the top panel 002, in a practical sense, it is sufficient if the positions of the subject in the respective captures coincide with each other to a certain degree. That is to say, a certain amount of displacement in position in the arrow P direction between the PET detectors 100 and the X-ray detector 202 is allowed. Therefore, the PET detectors 100 and the X-ray detector 202 can be arranged at substantially the same positions in the arrow P direction inside the same gantry 001. For example, it is sufficient if a range in the arrow P direction of the PET detector 100 overlaps a range of the X-ray detector 202 in the longer direction of the top panel 002.

Next, referring to FIG. 3, the capture of an X-ray CT image and a PET image by the PET device according to the present embodiment will be described. FIG. 3 is a flow chart of the capture of an X-ray CT image and a PET image by the PET device according to the present embodiment.

Step 001: The operator administers an agent to the subject and thereafter places the subject on the top panel 002.

Step 002: The driver 004 moves the top panel 002 to move the subject within the gantry 001.

Step 003: The gantry 001 rotates and the X-ray tube 201 irradiates an X-ray to the subject.

Step 004: The X-ray detector 202 detects the X-ray.

Step 005: The X-ray CT image reconstruction part 105 generates an X-ray CT image.

Step 006: The X-ray CT image reconstruction part 105 determines whether the capture of the X-ray CT image is finished based on the previously inputted capture plan. When the capture of the X-ray CT image is completed (Yes), the process proceeds to Step 007.

When the capture of the X-ray CT image is not completed yet (No), the process returns to Step 002.

Step 007: The driver 004 moves the top panel 002 in the opposite direction to a direction for capturing the X-ray CT image to move the subject within the gantry 001.

Step 008: The gantry 001 rotates and the PET detectors 100 detect the γ-rays.

Step 009: The PET image reconstruction part 104 generates a PET image.

Step 010: The PET image reconstruction part 104 determines whether the capture of the PET image is completed based on the previously inputted capture plan. When the capture of the PET image is completed (Yes), the capture of the image is ended. When the capture of the PET image has not yet been completed (No), the process returns to Step 007.

In the flow chart of FIG. 3, in order to save time, an advancing direction in the capture of a PET image is set opposite to an advancing direction in the capture of an X-ray CT image. However, as described above, another configuration may be employed. For example, it is possible to configure to, after completing the capture of an X-ray CT image, once return the top panel to the start position in the capture of the X-ray CT image, and capture a PET image in the same advancing direction as in the capture of the X-ray CT image.

[Second Embodiment]

A PET device according to the present embodiment differs from the aforementioned embodiment in that a semiconductor detector is used in the PET detector 100.

A semiconductor detector is a detector that detects radiation by utilizing such a phenomenon that an electric charge is generated when radiation enters a semiconductor. The semiconductor detector according to this embodiment is a device that directly converts the inputted γ-rays into electric signals.

The semiconductor detector of the PET detector 100 receives the incident γ-rays having been generated from the subject. Then, the semiconductor detector of the PET detector 100 converts the incident γ-rays into electric signals. Then, the PET detector 100 outputs the generated electric signals to the coincidence circuit 101.

The operation of each functional part after the coincidence circuit 101 receives input of the electric signals from the PET detector 100 is similar to that in the aforementioned embodiment.

An effect of use of the semiconductor detector in the PET detector 100 will be described.

The scintillator array used in the aforementioned embodiment is composed of a scintillator and a photo multiplier tube. The scintillator converts the inputted γ-rays into light. Then, the photo multiplier tube converts the light inputted from the scintillator into electric signals.

Since the scintillator array once converts radiation into light and then converts the light into electric signals, the scintillator array is called an indirect-conversion-type detector. On the other hand, since the semiconductor detector directly converts radiation into electric signals, the semiconductor detector is called a direct-conversion-type detector.

Since the scintillator array is composed of two parts, namely, a photo multiplier tube and a scintillator, the scintillator array has a complicated configuration and a large size. On the other hand, the semiconductor detector has a simple configuration, and can be easily miniaturized. Accordingly, the semiconductor can be easily arranged within the gantry 001 when used in the PET detector 100.

Further, the scintillator array has a bonding wire. The bonding wire is an easily cut part, and the bonding wire may be broken when the gantry 001 rotates. On the other hand, the semiconductor detector does not have a bonding wire, and is excellent in gravity resistance. In other words, use of the semiconductor detector can reduce the risk of breakage of the PET detector 100 when the gantry 001 rotates.

Furthermore, resolution of the semiconductor detector is higher than that of the scintillator array. Therefore, in the case of using the semiconductor detector in the PET detector 100, it is possible to generate a clearer PET image than in the case of using the scintillator array.

As described above, in the PET device according to the present embodiment, the PET detectors are arranged on substantially the same circumference as the X-ray tube and the X-ray detector. This makes the bend of the top panel substantially equal in both capture of a PET image and capture of an X-ray CT image. That is to say, when capturing a PET image and capturing an X-ray CT image, it is possible to capture at substantially the same positions of the subject. Therefore, the positions of the subject displayed in the X-ray CT image and the PET image are substantially identical. Accordingly, it is possible to solve an issue of displacement caused by the bend of the top panel when superimposing the X-ray CT image and the PET image, and it is possible to generate an accurate PET/CT fusion image. Consequently, the PET device according to the present embodiment can contribute to an accurate diagnosis of a cancer site by a physician or the like.

Further, the PET device according to the present embodiment is provided with the PET detectors in two regions within the gantry and configured to capture a PET image while rotating the gantry.

Consequently, it is possible to decrease the number of the detectors, and it is easy to reduce the cost and to uniformly mange the properties of the detectors. Moreover, the time required for investigation when the PET detector fails may be shortened.

Furthermore, by rotating the gantry, it is possible to detect the γ-rays at 360° on the entire circumference with the PET detectors arranged in two separate regions. That is, it is possible to generate a PET image having the same accuracy as in the case of the PET detector arranged on the entire circumference inside the gantry. In addition, since the PET detector and the X-ray detector can be arranged inside one gantry, it is possible to save space.

What is claimed is:

1. A PET device comprising:
   a top panel on which a subject to which an agent labeled with positron-emitting nuclides have been administered is placed;
   a cylindrical gantry configured to rotate around the subject about a body axis of the subject;
   an X-ray irradiating part arranged inside the gantry and configured to irradiate an X-ray;
   an X-ray detector arranged at a position facing the X-ray irradiating part inside the gantry and configured to detect the X-ray having been transmitted through the subject;
   two PET detectors arranged in two regions facing a rotation center inside the gantry and configured to detect γ-rays emitted from the positron-emitting nuclides;
   a moving mechanism configured to move the top panel and the gantry relatively to each other;
   an X-ray CT image generator configured to generate an X-ray CT image of an inside of the subject based on a result of detection by the X-ray detector; and
   a PET image generator configured to generate a PET image of the inside of the subject based on the γ-rays detected by the PET detectors on a circumference in accordance with rotation of the gantry, wherein
   the X-ray CT image of the inside of the subject is captured after the moving mechanism displaces the top panel and the PET image of the inside of the subject is captured after the moving mechanism displaces the top panel, the capturing timing of the X-ray CT image being different from the capturing timing of the PET image, and
   wherein the moving mechanism rotationally moves the gantry so that a mode of rotationally moving the gantry is different between capturing of the X-ray CT image and capturing of the PET image.

2. The PET device according to claim 1, wherein the X-ray detector and the PET detectors are arranged on substantially same circumferences and are sized so as not to overlap each other.

3. The PET device according to claim 2, further comprising a fusion part configured to superimpose the X-ray CT image based on data detected by the X-ray detector and the PET image based on γ-rays detected by the PET detectors to generate a PET/CT fusion image.

4. The PET device according to claim 3, wherein each of the PET detectors is composed of a semiconductor detector.

5. The PET device according to claim 4, wherein communication between the X-ray detector and the X-ray CT image generator and communication between the PET detectors and the PET image generator are performed via noncontact data transmission.

6. The PET device according to claim 3, wherein communication between the X-ray detector and the X-ray CT image generator and communication between the PET detectors and the PET image generator are performed via noncontact data transmission.

7. The PET device according to claim 2, wherein each of the PET detectors is composed of a semiconductor detector.

8. The PET device according to claim 7, wherein communication between the X-ray detector and the X-ray CT image generator and communication between the PET detectors and the PET image generator are performed via noncontact data transmission.

9. The PET device according to claim 2, wherein communication between the X-ray detector and the X-ray CT image generator and communication between the PET detectors and the PET image generator are performed via noncontact data transmission.

10. The PET device according to claim 1, further comprising a fusion part configured to superimpose the X-ray CT image based on data detected by the X-ray detector and the PET image based on γ-rays detected by the PET detectors to generate a PET/CT fusion image.

11. The PET device according to claim 10, wherein each of the PET detectors is composed of a semiconductor detector.

12. The PET device according to claim 11, wherein communication between the X-ray detector and the X-ray CT image generator and communication between the PET detectors and the PET image generator are performed via noncontact data transmission.

13. The PET device according to claim 10, wherein communication between the X-ray detector and the X-ray CT image generator and communication between the PET detectors and the PET image generator are performed via noncontact data transmission.

14. The PET device according to claim 1, wherein each of the PET detectors is composed of a semiconductor detector.

15. The PET device according to claim 14, wherein communication between the X-ray detector and the X-ray CT image generator and communication between the PET detectors and the PET image generator are performed via noncontact data transmission.

16. The PET device according to claim 1, wherein communication between the X-ray detector and the X-ray CT image generator and communication between the PET detectors and the PET image generator are performed via noncontact data transmission.

17. The PET device according to claim 1, wherein the mode of rotating the gantry for capturing the PET image is a mode of repeating rotating and stopping of the gantry, and the PET detector is configured to detect the γ-rays when the gantry stops.

18. The PET device according to claim 1, wherein the moving mechanism is configured to displace the top panel so that a moving direction of the top panel becomes opposite between the timing of capturing the X-ray image and the timing of capturing the PET image.

* * * * *